United States Patent [19]

Boberg et al.

[11] Patent Number: 4,943,568
[45] Date of Patent: Jul. 24, 1990

[54] CEPHALOSPORINS

[75] Inventors: Michael Boberg; Rolf Angerbauer; Karl G. Metzger, all of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 933,729

[22] Filed: Nov. 21, 1986

[30] Foreign Application Priority Data

Nov. 21, 1985 [DE] Fed. Rep. of Germany ....... 3541095

[51] Int. Cl.$^5$ ................. C07D 501/46; A61K 31/545
[52] U.S. Cl. .................................... 514/206; 514/207; 514/209; 540/222; 540/225; 540/227
[58] Field of Search ............. 540/225, 227, 222; 514/206, 207, 209

[56] References Cited

U.S. PATENT DOCUMENTS 4,416,880 11/1983 Boberg et al. ..................... 540/227

FOREIGN PATENT DOCUMENTS 0082498 6/1983 European Pat. Off. .
0164944 12/1985 European Pat. Off. .

OTHER PUBLICATIONS

Chemical Abstracts, vol. 108, 221491m (1988), Abstracting Kokai Japan 62, 215 593 (1987).

Primary Examiner—Nicholas S. Rizzo
Attorney, Agent, or Firm—Sprung Horn Kramer & Woods

[57] ABSTRACT

Antibacterially active novel cephalosporins of the formula

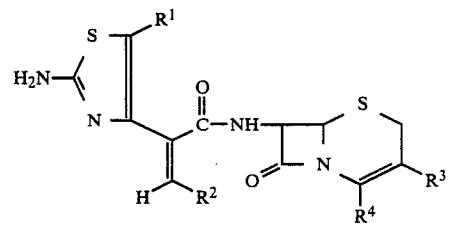

in which $R^1$ represents alkyl, alkenyl, alkoxy, alkylthio, halogen, trifluoromethyl or trifluoromethoxy, $R^2$ represents hydrogen or an organic radical, $R^3$ represents hydrogen, alkyl, alkenyl, alkoxy, alkylthio, halogen, hydroxymethyl or ethers or esters thereof, or various organothiomethyl or substituted aminomethyl radicals, and $R^4$ represents COO$^-$ or COOH, or salts thereof.

6 Claims, No Drawings

CEPHALOSPORINS

The invention relates to new cephalosporins, processes for their preparation and their use in medicaments, in particular in antibacterial therapy.

Cephalosporins which carry an unsubstituted aminothiazolyl radical as acyl side chain are known from European Patent No. A-49,448.

The present invention relates to new cephalosporins of the general formula (I)

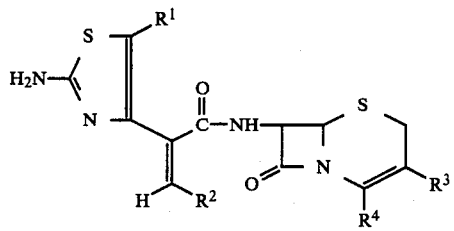

in which
R$^1$ represents alkyl, alkenyl, alkoxy, alkylthio, halogen, trifluoromethyl or trifluoromethoxy,
R$^2$ represents hydrogen, or represents alkenyl, or represents optionally substituted alkyl, optionally substituted aryl, optionally substituted heterocyclyl, alkoxy, carboxyl, alkoxycarbonyl or halogen, or represents a group of the formula —S(O)$_n$—B—A, wherein
n denotes 0, 1 or 2,
B represents a direct bond, oxygen or a group —N—X and
A and X independently of one another represent hydrogen, optionally substituted alkyl, optionally substituted aryl or optionally substituted heterocyclyl, or together form an optionally substituted carbocyclic or heterocyclic ring,
R$^3$ represents hydrogen, alkyl, alkenyl, alkoxy, alkylthio or halogen, or represents a group of the formula —CH$_2$—Y, wherein
Y represents hydroxyl, formyloxy, alkanoyloxy or aminocarbonyloxy, or represents optionally substituted heterocyclylthio, or represents a 6-membered ring which contains nitrogen, is bonded via N, is positively charged and contains a total of up to three nitrogen atoms, and onto which up to two further rings can be fused and which can optionally be substituted, or represents a group of the formula

wherein
R$^5$, R$^6$ and R$^7$ can be identical or different and denote a substituted or unsubstituted alkyl radical or a mono- or bicyclic, optionally substituted carbo-or heterocyclic ring, or
R$^5$ represents an optionally substituted alkyl radical or a mono- or bicyclic, substituted or unsubstituted carbo- or heterocyclic ring and
R$^6$ and R$^7$, together with the N atom, form an optionally substituted mono- or polycyclic ring, which can be saturated or unsaturated and can contain oxygen, sulphur and/or nitrogen as further heteroatoms, and
R$^4$—depending on the meaning of R$^3$—represents COO$^-$ or COOH,
and salts thereof.

The compounds of the formula (I) can be in the form of free acids, esters, inner salts or non-toxic pharmaceutically acceptable salts of the acid carboxyl groups, such as sodium, potassium, magnesium, calcium, aluminum and ammonium salts and non-toxic substituted ammonium salts, with amines, such as di- and tri-lower alkylamines, procaine, dibenzylamine, N,N'-dibenzylalkylenediamine, N-benzyl-$\beta$-phenylethylamine, N-methyl-and N-ethylmorpholine, 1-ephenamine, dehydroabietylamine, N,N'-bis-dehydroabietylethylenediamine, N-lower alkyl piperidines and other amines which can be used to form salts of penicillins and cephalosporins.

The definition of alkyl in each case includes straight-chain or branched, optionally substituted radicals with up to 18 C atoms, preferably with up to 10 C atoms and in particular with up to six C atoms, it also being possible for these radicals to be carbocyclic.

Preferred compounds are those in which
R$^1$, R$^2$ and R$^4$ have the meaning given and
R$^3$ represents hydrogen, alkyl, alkenyl, alkoxy, alkylthio or halogen, or represents a group of the formula —CH$_2$—Y, wherein
Y represents hydroxyl, formyloxy, alkanoyloxy or aminocarbonyloxy, or represents optionally substituted heterocyclylthio, or represents a pyridinium radical,

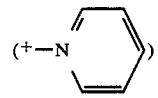

which can optionally be mono- or polysubstituted by identical or different substituents and onto which one or two optionally substituted three- to seven-membered rings, each of which can contain up to two hetero atoms and up to two double bonds and can also be aromatic or heteroaromatic, can be fused, or represents a radical of the formula

wherein
R$^5$, R$^6$ and R$^7$ are identical or different and represent an optionally substituted C$_1$–C$_6$-alkyl radical or a three-to seven-membered optionally substituted ring, or
R$^5$ has the above meaning and
R$^6$ and R$^7$, together with the N atom, form a three-to seven-membered ring, which can be saturated or unsaturated, can be mono- or polysubstituted, preferably mono-, di- or trisubstituted, by identical or different substituents and can contain one or two further heteroatomns, which can be oxygen, nitrogen and/or sulphur.

If R$^1$ represents alkyl, alkoxy or alkylthio, this is preferably straight-chain or branched lower alkyl, lower alkoxy or lower alkylthio with in each case up to about 6 C atoms.

If $R^2$ represents an alkyl radical, this is preferably a straight-chain or branched, optionally substituted radical with up to 18 C atoms, particularly preferably with up to 12 C atoms and in particular with up to 6 C atoms. Alkyl in the context of this definition also includes carbocyclic radicals.

If the alkyl radical $R^2$ is substituted, it is preferably substituted by one or two substituents, preferably from the group comprising halogen, hydroxyl, lower alkoxy, oxo, thio, nitro, cyano, carboxyl, lower alkoxycarbonyl, aminocarbonyloxy, sulpho, aryl, lower alkanoyloxy, $S(O)_m-R^8$ or

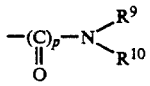

wherein
m represents 0, 1 or 2,
p represents 0 or 1,
$R^8$ represents lower alkyl or phenyl and
$R^9$ and $R^{10}$ independently of one another represent hydrogen or together or individually represent lower alkyl or lower alkanoyl.

If $R^2$ represents an aryl radical, this is preferably a radical of the formula

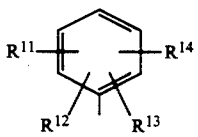

wherein
$R^{11}$, $R^{12}$, $R^{13}$ and $R^{14}$ independently of one another denote hydrogen, halogen, optionally substituted lower alkyl, phenyl, lower alkanoyl, amino, lower alkyl amino, di-lower alkylamino, lower alkanoylamino, nitro, cyano, lower alkoxy, lower alkylthio, carboxyl, lower alkoxycarbonyl, aminocarbonyloxy, sulpho or phenylsulphonyl or lower alkylsulphonyl.

If $R^2$ represents a heterocyclic radical, this is preferably a five- or six-membered ring with 1-4 identical or different hetero atoms from the group comprising N, O and S. Particularly preferred radicals here are pyridine, pyrimidine, pyrazine, pyridazine, furan, thiophene, isoxazole, thiazole, thiadiazole, triazole or quinoline radicals.

Preferred substituents on a heterocyclic radical in $R^2$ are lower alkyl, phenyl, halogen, lower alkanoyl, lower alkoxy, lower alkylthio, nitro, cyano, amino, lower alkylamino, carboxyl, lower alkoxycarbonyl, aminocarbonyloxy, sulpho, phenylsulphonyl and lower alkylsulphonyl.

If $R^2$ represents alkoxy or alkoxycarbonyl, this is preferably lower alkoxy with up to about 8 C atoms or lower alkoxycarbonyl with up to about 8 C atoms.

If $R^2$ represents a group of the formula $-S(O)_n-B-A$, n preferably denotes 0, 1 or 2, B preferably denotes oxygen, a direct bond or the group $-NX-$, and A and X preferably independently of one another represent hydrogen, alkyl, aryl or heterocyclyl, with the meaning already given, or A and X together preferably form an optionally substituted five- to six-membered carbocyclic or heterocyclic ring from the group: pyrrolidine, piperidine, piperazine, morpholine and thiomorpholine.

If $R^3$ represents alkyl, alkenyl, alkoxy or alkylthio, this is in each case lower alkyl, lower alkenyl, lower alkoxy or lower alkylthio with in each case up to 8 C atoms, it being possible for the alkyl radicals and the alkenyl radicals to be straight-chain or branched.

If $R^3$ represents the group $-CH_2-Y$ and Y denotes optionally substituted heterocyclylthio, Y preferably represents thiadiazolyl, triazolyl, triazinone or tetrazolyl bonded via a sulphur atom, possible substituents being optionally lower alkyl, carboxy-lower alkyl, sulpho-lower alkyl, carbamoyl-lower alkyl, sulphonamidolower alkyl, hydroxy-lower alkyl, dimethylamino-lower alkyl or diethylamino-lower alkyl with in each case up to eight C atoms in the alkyl radical.

If Y in $R^3$ represents a ring which contains nitrogen, is bonded via N and is positively charged, this is preferably a pyridinium radical which is optionally mono- or polysubstituted, preferably mono-, di-or trisubstituted and in particular mono- or disubstituted, for example by $C_1-C_4$-alkyl, halogen, carbamoyl, N-$C_1-C_4$-alkylcarbamoyl, hydroxy-$C_1-C_4$-alkyl, such as, in particular, hydroxymethyl, hydroxyethyl, hydroxypropyl, hydroxyisopropyl, hydroxybutyl, hydroxy-sec.-butyl or hydroxy-tert.-butyl, it also being possible for the alkyl radical to carry two or three hydroxyl groups, carboxy-$C_1-C_4$-alkyl, such as, in particular, carboxymethyl and carboxyethyl, $C_1-C_4$-alkoxycarbonyl-$C_1-C_4$-alkyl, such as, in particular, methoxycarbonylmethyl, ethoxycarbonylmethyl or methoxycarbonylethyl, formyl-$C_1-C_4$-alkyl, such as, in particular, formylethyl, $C_1-C_4$-alkylcarbonyl-$C_1-C_4$-alkyl, such as, in particular, methylcarbonylmethyl, ethylcarbonylmethyl, methylcarbonylethyl and ethylcarbonylethyl, it also being possible for the two alkyl groups of these to be further substituted by hydroxyl and it also being possible for the carbonyl groups of these to be in ketalized form, $C_1-C_4$-alkyl which is substituted by carbamoyl such as, in particular, carbamoylmethyl and carbamoylethyl, which can also be further substituted by hydroxyl on the nitrogen, such as, in particular, N-hydroxycarbamoylmethyl, sulpho-$C_1-C_4$-alkyl, such as, in particular, sulphoethyl or 1-hydroxy-1-sulphomethyl, $C_1-C_4$-alkoxy-$C_1-C_4$-alkyl, such as, in particular, methoxymethyl, ethoxymethyl, propoxymethyl, isopropoxymethyl, methoxyethyl, ethoxyethyl, methoxypropyl and methoxyisopropyl, which can also be substituted by hydroxyl, such as, in particular, hydroxymethoxymethyl and hydroxyethoxymethyl, $C_1-C_4$-alkylthio-$C_1-C_4$-alkyl, such as, in particular, methylthiomethyl, ethylthiomethyl, methylthioethyl and ethylthioethyl, $C_1-C_4$-alkylsulphinyl-$C_1-C_4$-alkyl, such as, in particular, methylsulphinylmethyl, ethylsulphinylmethyl, methylsulphinylethyl, and ethylsulphinylethyl, $C_1-C_4$-alkylsulphonyl-$C_1-C_4$-alkyl, such as, in particular, methylsulphonylmethyl, ethylsulphonylmethyl, methylsulphonylethyl and ethylsulphonylethyl, $C_3$-alkenyloxy-$C_1-C_4$-alkyl, such as, in particular, allyloxymethyl and allyloxyethyl, $C_3$-alkenylthio-$C_1-C_4$-alkyl, such as, in particular, allylthiomethyl, $C_3$-alkenylsulphinyl-$C_1-C_4$-alkyl, such as, in particular, allylsulphinylmethyl, $C_3$-alkenylsulphonyl-$C_1-C_4$-alkyl, such as, in particular, allylsulphonylmethyl, cyano-$C_1-C_3$-alkyl, such as, in particular, cyanomethyl or cyanoethyl, epoxy-$C_1$–$C_3$-alkyl, such as, in particular, epoxyethyl or epoxypropyl, trifluoromethyl, hydroxyiminomethyl or $C_1$–$C_3$-alkyloximinomethyl, such as, in particular, methoxyiminomethyl, $C_3$–$C_4$-alkenyl, such as, in particular, allyl, 2-methylallyl and buten-3-yl, which can also be further substituted by hydroxyl, such as, in particular, hydroxyallyl and hydroxybutenyl, $C_3$-alkynyl, such as, in particular, propargyl, $C_3$–$C_6$-cycloalkyl or $C_3$–$C_6$-cycloalkyl-methyl, such as, in particular, cyclopropyl, cyclobutyl, cyclopentyl, cyclohexyl or cyclopentylmethyl, it also being possible for the rings to be substituted, for example by hydroxyl, such as, in particular, 1-hydroxy-1-cyclopentyl and 1-hydroxy-1-cyclohexyl, or by halogen, preferably chlorine, or by carboxyl, $C_1$–$C_4$-alkoxycarbonyl or cyano, $C_5$–$C_6$-cycloalkenyl, such as, in particular, cyclopenten-1-yl or cyclohexen-1-yl, $C_1$–$C_4$-alkoxy, such as, in particular, methoxy, ethoxy, propoxy, isopropoxy, butoxy, isobutoxy or tert.-butoxy, preferably methoxy, it also being possible for these alkoxy groups to be further substituted, for example by hydroxyl, carboxyl or $C_1$–$C_4$-alkoxycarbonyl, in particular carboxymethoxy or methoxycarbonylmethoxy, epoxy-$C_2$–$C_3$-alkoxy, such as, in particular, epoxyethoxy or epoxypropoxy, $C_3$-alkenyloxy, such as, in particular, allyloxy, $C_3$-alkynyloxy, such as, in particular, propargyloxy, aryloxy, such as, in particular, phenoxy, amino, $C_1$–$C_5$-alkylamino, such as, in particular, ethylamino, $C_1$–$C_5$-dialkylamino, such as, in particular, dimethylamino or diethylamino, $C_1$–$C_4$ alkoxycarbonylamino, such as, in particular, methoxycarbonylamino or ethoxycarbonylamino, $C_1$–$C_4$-alkylcarbonylamino, such as, in particular, methylcarbonylamino, N-$C_1$–$C_4$-alkyl- or dialkylcarbamoylamino, such as, in particular, N-methylcarbamoylamino or N,N-diethylcarbamoylamino, $C_1$–$C_4$-alkylsulphonylamino, such as, in particular, methyl-or ethylsulphonylamino, cyano, hydroxyl, in particular 3-hydroxy, $C_1$–$C_4$-alkylthio, such as, in particular, methylthio, ethylthio, propylthio or isopropylthio, which can also be substituted by hydroxyl, in particular hydroxyethylthio, $C_1$–$C_4$-alkylsulphinyl, such as, in particular, methylsulphinyl, ethylsulphinyl, propylsulphinyl or isopropylsulphinyl, which can also be substituted by hydroxyl, in particular hydroxyethylsulphinyl, $C_1$–$C_4$-alkylsulphonyl, such as methyl-, ethyl-, propyl- or isopropylsulphonyl, which can also be substituted by hydroxyl, in particular hydroxyethylsulphonyl, carboxymethylthio or $C_1$–$C_4$-alkoxycarbonylmethylthio, in particular methoxycarbonylmethylthio, carboxymethyl-sulphinyl or -sulphonyl, and $C_1$–$C_4$-alkoxycarbonylmethylsulphinyl or -sulphonyl, in particular methoxycarbonylmethylsulphinyl or -sulphonyl, 3-alkenylthio, such as allylthio or propen-1-yl-thio, $C_3$-alkenylsulphinyl, such as allylsulphinyl and propen-1-yl-sulphinyl, $C_3$-alkenylsulphonyl, such as allylsulphonyl or propen-1-yl-sulphonyl, phenyl or benzyl, which can also be substituted, for example by halogen, in particular chlorine, such as, for example, 4-chlorobenzyl, 2'-thienyl or 3'-thienyl, formyl or ketalized formyl, such as, for example, 1,3-dioxolan-2-yl, $C_1$–$C_4$-alkylcarbonyl, in particular acetyl or propionyl, preferably acetyl, which can also be substituted by hydroxyl and can be in ketalized form, such as, for example, 2-methyl-1,3-dioxolan-2-yl, benzoyl, $C_1$–$C_4$-alkylcarbonylamino, in particular acetylamino or propionylamino, formylamino, carboxyl or $C_1$–$C_4$-alkoxycarbonyl, in particular methoxycarbonyl or ethoxycarbonyl, and onto which an optionally substituted 5- or 6-membered ring, which can contain up to two heteroatoms, preferably from the group comprising O, N and S, and up to two double bonds and which can also be aromatic or heteroaromatic, can be fused. Possible fused-on rings are, in particular, the following ring systems: cyclopenteno, dihydrocyclopenteno, cyclohexeno, dihydrocyclohexeno, benzo, furo, dihydrofuro, pyrano, dihydropyrano, thieno, dihydrothieno, thiopyrano, dihydrothiopyrano, pyrido, dihydropyrido, tetrahydropyrido, pyrimido, dihydropyrimido, tetrahydropyrimido, pyrazino, dihydropyrazino, tetrahydropyrazino, pyridazino, dihydropyridazino or tetrahydropyridazino, each of which can be mono- or polysubstituted, but preferably monosubstituted, preferably by $C_1$–$C_4$-alkyl, such as, in particular, methyl, ethyl or isopropyl, $C_3$–$C_6$-cycloalkyl, such as, in particular, cyclopropyl, $C_1$–$C_4$-alkoxy, such as, in particular, methoxy or ethoxy, $C_1$–$C_3$-hydroxyalkyl, such as, in particular, hydroxymethyl or hydroxyethyl, halogen, such as, in particular, chlorine or fluorine, hydroxyl, carboxyl or cyano, $C_1$–$C_6$ alkoxycarbonyl, such as, in particular, methoxycarbonyl or ethoxycarbonyl, oxo or hydroximino, carbamoyl or sulphamoyl, amino, $C_1$–$C_4$-alkylamino, such as, in particular, methylamino or ethylamino, or $C_1$–$C_4$-dialkylamino, such as, in particular, diethylamino.

If Y represents the group

and $R^5$ and/or $R^6$ and/or $R^7$ represent a substituted alkyl radical, this is preferably substituted by one or two substituents from the series comprising hydroxyl, carboxyl, lower alkoxycarbonyl, aminocarbonyl, lower alkylaminocarbonyl, formyl and lower alkanoyl, the carbonyl group of which can also be in ketalized form, oxo, thio, sulpho, cyano, nitro, amino, halogen, lower alkylamino, di-lower alkylamino, lower alkanoylamino, aminocarbonylamino, lower alkylsulphonyl, phenyl, heterocyclyl and heteroaryl.

If $R^5$ and/or $R^6$ and/or $R^7$ represent a saturated or unsaturated optionally substituted three- to seven-membered ring, this is preferably a carbo- or heterocyclic ring which can contain up to three, preferably one or two, heteroatoms, which can be oxygen, nitrogen and/or sulphur.

If the ring is substituted, it is preferably substituted by one or two substituents from the series comprising lower alkyl, hydroxyl, hydroxy-lower alkyl, carboxyl, lower alkoxycarbonyl, formyl and lower alkanoyl, the carbonyl groups of which can also be in ketalized form, carbamoyl, sulpho, cyano, nitro, amino, halogen, lower alkylamino, di-lower alkylamino, lower alkanoylamino, lower alkoxy, lower alkylthio, lower alkylsulphinyl, lower alkylsulphonyl, phenyl, heterocyclyl and heteroaryl.

If $R^6$ and $R^7$ together with the N atom form an optionally substituted heterocyclic ring, this is preferably a three- to seven-membered ring which can contain one or two double bonds and up to two further hetero atoms, which can be oxygen, nitrogen or sulphur, and onto which a further five- to six-membered ring can be fused.

If the heterocyclic ring formed by $R^6$ and $R^7$ together with the N atom is substituted, it is preferably substituted by one or two substituents from the series comprising lower alkyl, hydroxyl, hydroxy-lower alkyl, carboxyl, lower alkoxycarbonyl, formyl and lower alkanoyl, the carbonyl groups of which can also be in ketalized form, sulphamoyl, carbamoyl, sulpho, cyano, nitro, amino, halogen, lower alkylamino, di-lower alkylamino, lower alkanoylamino, lower alkoxy, lower alkylthio, lower alkylsulphinyl, lower alkylsulphonyl, aryl, heteroaryl and heterocyclyl.

The meaning of aryl in the context of this definition has already been given for $R^2$.

The radicals heterocyclyl and heteroaryl in the context of this definition preferably denote: pyridyl, pyrimidyl, pyridazinyl, pyrazinyl, thienyl, furyl, isoxazolyl, thiazolyl, piperazinyl, piperidinyl, pyrrolidinyl, morpholinyl, imidazolyl or quinolyl.

Halogen in the context of the invention preferably denotes fluorine, chlorine or bromine.

Particularly preferred compounds of the formula (I) are those in which $R^1$ represents $C_1$-$C_4$-alkyl, $C_1$-$C_4$-alkoxy, fluorine, chlorine, bromine or trifluoromethyl, $R^2$ represents $C_1$-$C_4$-alkyl, which is optionally substituted by hydroxyl, fluorine, chlorine, carboxyl, $C_1$-$C_4$-alkoxycarbonyl, $C_1$-$C_4$-alkylsulphonyl or carbamoyloxy, or represents cyclopentyl or cyclohexyl, or represents phenyl, which is optionally substituted by fluorine, chlorine, $C_1$-$C_4$-alkyl, $C_1$-$C_4$-alkoxy, $C_1$-$C_4$-alkylthio, carboxy, $C_1$-$C_4$-alkoxycarbonyl, di-$C_1$-$C_4$-alkylamino, cyano, nitro or sulpho, or represents pyridyl, thienyl, pyrimidyl, thiazolyl, diazolyl or thiadiazolyl, optionally substituted by $C_1$-$C_4$-alkyl, fluorine, chlorine, amino, di-$C_1$-$C_4$-alkylamino or acetylamino, or represents $C_1$-$C_4$-alkoxy, carboxyl, $C_1$-$C_4$-alkoxycarbonyl, fluorine, chlorine, $C_1$-$C_4$-alkylsulphonyl or phenylsulphonyl, $R^3$ represents hydrogen, $C_1$-$C_4$-alkyl, $C_1$-$C_4$-alkoxy, $C_2$-$C_4$-alkenyl, $C_1$-$C_4$-alkylthio, fluorine, chlorine or bromine, or represents a group of the formula —$CH_2$—Y, wherein Y represents hydroxyl, formyloxy, acetyloxy, methoxy, aminocarbonyloxy, or represents triazolyl, thiadiazolyl, triazinone or tetrazolyl, optionally substituted by methyl, carboxymethyl, sulphomethyl, dimethylaminoethyl or sulphamoylethyl, or represents a pyridinium radical, onto which a five- to six-membered ring from the series comprising cyclopenteno, cyclohexeno and benzo is optionally fused and which is optionally mono- or polysubstituted by substituents from the group comprising fluorine, chlorine, methyl, ethyl, carbamoyl, hydroxymethyl, hydroxyethyl, hydroxypropyl, carboxymethyl, carboxyethyl, methoxycarbonylmethyl, ethoxycarbonylmethyl, methoxycarbonylethyl, formylmethyl, formylethyl, methylcarbonylmethyl, carbamoylmethyl, carbamoylethyl, sulphomethyl, sulphoethyl, methoxymethyl, ethoxymethyl, methoxyethyl, methylthiomethyl, methylsulphinylmethyl, methylsulphinylethyl, methylsulphonylmethyl, methylsulphonylethyl, ethylsulphonylmethyl, allyloxymethyl, cyanomethyl, cyanoethyl, trifluoromethyl, allyl, cyclopropyl, cyclopentyl, cyclohexyl, cyclopentylmethyl, methoxy, ethoxy, propoxy, isopropoxy, carboxymethoxy, allyloxy, phenoxy, amino, methylamino, ethylamino, dimethylamino, diethylamino, methoxycarbonylamino, acetylamino, methylsulphonylamino, cyano, hydroxy, methylthio, methylsulphinyl, methylsulphonyl, ethylsulphonyl, propylsulphonyl, phenyl, benzyl, chlorobenzyl, chlorophenyl, formyl, acetyl, formylamino, carboxy, methoxycarbonyl or ethoxycarbonyl, or represents a group of the formula

wherein $R^5$, $R^6$ and $R^7$ are identical or different and represent a $C_1$-$C_6$-alkyl radical, such as, in particular, methyl, ethyl, propyl, cyclopropyl, cyclopropylmethyl, cyclopentyl or cyclopentylmethyl, or represent a substituted $C_1$-$C_6$-alkyl radical, such as, in particular, hydroxymethyl, hydroxyethyl, hydroxypropyl, aminomethyl, aminoethyl, hydroxycarbonylmethyl, hydroxycarbonylethyl, cyanomethyl, nitromethyl, nitroethyl, methoxymethyl, methoxycarbonylmethyl or trifluoromethyl, or in which $R^5$ has the above meaning and $R^6$ and $R^7$, together with the N atom, form a five- to six-membered heterocyclic ring which can contain a further hetero atom and onto which a further ring can be fused, such as, in particular, pyrrolidinium, piperazinium, piperidinium, morpholinium, pyrrolinium, pyrazolidinium, indolinium, isoindolinium, oxazolidinium, thiazolidinium or thiomorpholinium, and which can optionally be substituted by $C_1$-$C_4$-alkyl, such as, in particular, methyl, ethyl or propyl, which can in turn be substituted, for example by hydroxyl, carboxyl, cyano, nitro, amino, halogen, alkoxy or $C_1$-$C_6$-alkylcarbonyl, such as, in particular, formyl or methyl- or ethylcarbonyl, or by carbamoyl, sulpho, cyano, nitro or halogen, such as, in particular, fluorine and chlorine, amino, $C_1$-$C_6$-alkyl or dialkylamino, such as, in particular, methylamino, dimethylamino or diethylamino, $C_1$-$C_6$-alkylcarbonylamino, such as, in particular, methylcarbonylamino or ethylcarbonylamino, $C_1$-$C_6$-alkoxy, such as, in particular, methoxy, $C_1$-$C_6$-alkylthio, such as, in particular, methylthio, $C_1$-$C_6$-alkylsulphinyl, such as, in particular, methylsulphinyl, or $C_1$-$C_6$-alkylsulphonyl, such as, in particular, methyl- or ethyl-sulphonyl, or by aryl, such as, in particular, phenyl or naphthyl, which can also be substituted, or by hetaryl, such as pyridyl, which can also be substituted, and $R^4$—depending on the meaning of $R^3$—represents COOH or COO$^-$, and salts thereof.

Especially preferred compounds of the formula (I) are those in which $R^1$ represents methyl, fluorine, chlorine or trifluoromethyl, $R^2$ represents methyl, ethyl, propyl, isopropyl, trifluoromethyl, carboxymethyl, methoxycarbonylmethyl, cyclopentyl or cyclohexyl, or represents phenyl, chlorophenyl or carboxyphenyl, or represents pyridyl or aminothiazolyl, or represents carboxyl, or represents methoxy, ethoxy, methylthio, methylsulphonyl, ethylsulphonyl, phenylsulphonyl, fluorine or chlorine, $R^3$ represents hydrogen, chlorine, fluorine, methyl, methoxy, methylthio, trifluoromethyl or vinyl, or represents the group of the formula —CH₂—Y, wherein Y represents methoxy, methylcarbonyloxy, carbamoyloxy or a radical of the formula

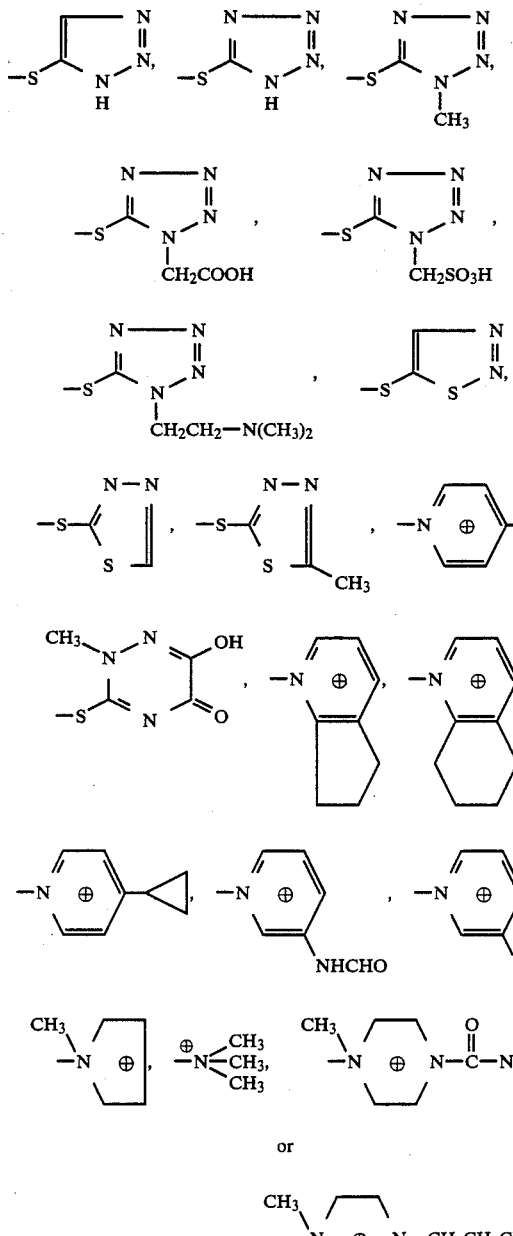

and
$R^4$ represents COOH or COO⁻,
and salts thereof.

The compounds of the general formula (I) are obtained by a process in which compounds of the general formula (II)

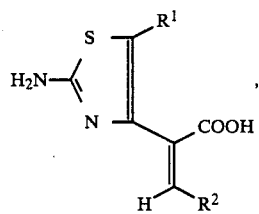

in which
$R^1$ and $R^2$ have the meaning given,
in which compounds the amino group can be protected or unprotected, after activation of the carboxyl group by conversion into a mixed anhydride, for example with ethyl chloroformate or methanesulphonyl chloride, after conversion into the acid halide or after conversion into an activated ester with, for example, N-hydroxybenzotriazole or dicyclohexylcarbodiimide, are reacted with compounds of the general formula (III)

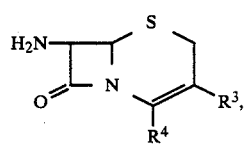

in which
$R^3$ and $R^4$ have the abovementioned meaning,
and, if appropriate, protective groups are split off and the desired salts are prepared or the free acids are prepared from salts.

A large number of methods known from cephalosporin or penicillin chemistry can be used for coupling carboxylic acids (II) to β-lactams of the formula (III). It has proved advantageous to activate the carboxylic acids of the general formula (II) without an amine-protective group and then to couple the activated compounds with the β-lactams of the formula (III), which have been dissolved as salts with an amine. It is particularly advantageous to carry out the activation with sulphonic acid derivatives of the formula (IV) to give anhydrides of the formula (V)

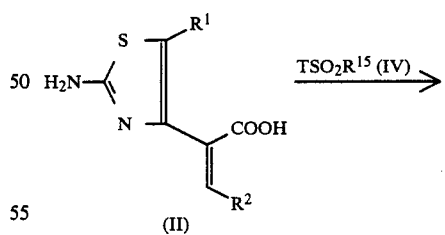

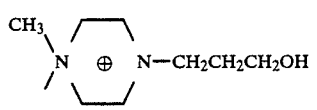

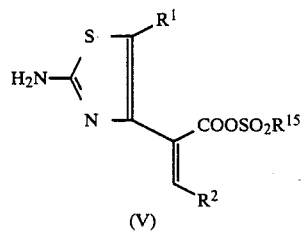

wherein
T represents a radical $R^{15}$—SO₂O or halogen and $R^{15}$ represents an alkyl radical which has 1 to 10 C atoms and can optionally be substituted by fluorine, chlorine, cyano, phenyl, alkoxycarbonyl, alkoxy or alkyl, it being possible for the latter alkyl radicals to carry 1 to 4 C atoms, or a phenyl radical, which can optionally be substituted by fluorine, chlorine, bromine, cyano, alkyl, alkoxy, alkylthio, alkylcarbonyl—it being possible for the latter alkyl groups to carry 1 to 4 C atoms—nitro, trifluoromethyl or phenyl.

If $R^{15}$ is substituted, one to three substitutents, preferably those mentioned, are preferably present.

$R^{15}$ especially preferably represents a methyl or p-tolyl radical.

The mixed anhydrides of the formula (V) are prepared by a process in which the carboxylic acids of the formula (II) and 1–1.4 equivalents of an amine are dissolved in a solvent and allowed to react with 1 to 1.2 equivalents of a sulphonic acid derivative of the formula (IV).

Suitable solvents are all the solvents which are stable under the reaction conditions, such as, for example, diethyl ether, tetrahydrofuran, acetonitrile, acetone, methylene chloride, chloroform or dimethylformamide.

Suitable amines are tertiary amines, such as, for example, triethylamine, tripropylamine or tributylamine, and also sterically hindered secondary amines, such as, for example, diisopropylamine, as well as mixtures of these amines.

The reactions can be carried out at temperatures between $-80°$ C. and room temperature, low temperatures avoiding isomerization of the substituents on the double bond. The activation is advantageously carried out with Cl—$SO_2$—$CH_3$ in dimethylformamide at $-40°$ to $-60°$ C. in the course of 0.2 to 24 hours, preferably 0.5 to 5 hours.

The solvents mentioned for the preparation of the compounds of the formula (V) and also water can be used to dissolve the compounds of the formula (III), and the base used can be the amines mentioned there.

Activation of the carboxylic acids of the general formula (II) by conversion into an activated ester with, for example, N-hydroxysuccinimide and dicyclohexylcarbodiimide or 1-hydroxybenzotriazole and dicyclohexylcarbodiimide, is also particularly advantageous.

Suitable solvents are all the solvents which are also suitable for the preparation of anhydrides of the formula (V).

The reactions can be carried out at temperatures between $-30°$ C. and $+100°$ C. Advantageously, activation is carried out with 1-hydroxybenzotriazole and dicyclohexylcarbodiimide in dimethylformamide at room temperature for two to six hours, the dicyclohexylurea which has precipitated is then filtered off with suction and the reaction with a compound of the formula (III) in the form of a solution of its amine salt is carried out in the course of two to 24 hours. The solvents mentioned for the preparation of the compounds of the formula (V) or water can be used to dissolve the compounds of the formula (III) and the base used can be the amines mentioned there.

The compounds of the general formula (IIIa)

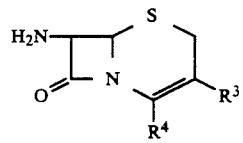
(IIIa)

in which
$R^3$ represents hydrogen, alkyl, alkenyl, alkoxy, alkylthio or halogen, or represents the group of the formula —$CH_2$—Y, wherein
Y represents hydroxyl, formyloxy, alkanoyloxy or aminocarbonyloxy, or represents optionally substituted heterocyclylthio, or represents a six-membered ring which contains nitrogen, is bonded via N, is positively charged and contains up to three nitrogen atoms, and onto which up to two further rings can be fused and which can optionally be substituted, and
$R^4$ represents $COO^-$ or COOH,
are known or can be prepared by known methods (C. W. Ryan et al., J. Med. Chem. 12, 310, U.S. Pat. No. 3,925,372, U.S. Pat. No. 3,994,884, DE-OS (German Published Specification) No. 2,506,194, EP-OS (European Published Specification) No. 144,032, DE-OS (German Published Specification) No. 3,013,545 and European Patent No. 65,748).

The compounds of the general formula (IIIb) in which
$R^3$ represents the group —$CH_2$—Y and
Y represents a radical of the formula

wherein
$R^5$, $R^6$ and $R^7$ can be identical or different and denote a substituted or unsubstituted alkyl radical or a mono- or bicyclic, optionally substituted carbo- or heterocyclic ring, or
$R^5$ represents an optionally substituted alkyl radical or a mono- or bicyclic substituted, carbo- or heterocyclic ring and
$R^6$ and $R^7$, together with the N atom, form an optionally substituted mono- or polycyclic ring which can be saturated or unsaturated and can contain oxygen, sulphur or nitrogen as further heteroatoms, and
$R^4$ represents $COO^-$,
are obtained by a process in which, from compounds of the formula (VI)

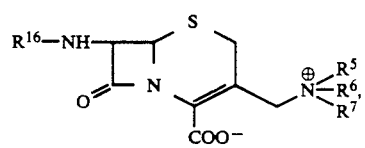
(VI)

in which
$R^5$, $R^6$ and $R^7$ have the meaning given, the amino protective group $R^{16}$ is split off (VI→III). $R^{16}$ here can be either a protective group which is unstable towards acids, such as the tert.-butoxycarbonyl group, or, advantageously, a protective group which can be split off enzymatically. Preferred protective groups which can be split off enzymatically are phenacetyl or 2-thienylacetyl. Enzymatic splitting off is carried out at room temperature in water or a mixture of water and a polar organic solvent, such as, for example, acetonitrile or tetrahydrofuran, with immobilized penicillin G acylase at pH 7–8, preferably at pH 7.5–7.8. During the splitting off, the pH value is kept constant by addition of a base, such as lithium hydroxide, sodium hydroxide or potassium hydroxide, or of a tertiary amine, for example triethylamine, tripropylamine, tributylamine or pyridine.

The compounds of the formula (VI) can be prepared from esters of the formula (VII) via intermediate compounds of the formula (VIII).

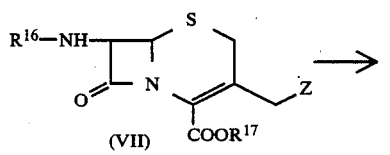

(VII)   COOR$^{17}$

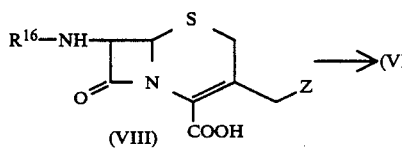

(VIII)   COOH   →(VI)

In the esters of the formula (VII), Z represents a leaving group, such as mesylate, tosylate, brosylate, triflate, nonaflate, iodide, bromide or chloride, and $R^{17}$ represents an acid-protective group customary in cephalosporin chemistry, preferably a protective group which can be split off under acid conditions, such as, for example, benzhydryl, bis-(4-methoxyphenyl)-methyl or tert.-butyl.

The compounds of the formula (VII) are converted into the reactive free acids of the formula (VIII) by splitting off the acid-protective group $R^{17}$. In the case of the preferred protective groups $R^{17}$ which are unstable towards acids, the protective group is split off in an organic solvent. Splitting off of the benzhydryl protective group in methylene chloride with trifluoroacetic acid, possibly with the addition of an alkoxybenzene, preferably methoxybenzene, is preferred. The splitting off is carried out at $-20°$ C. to $+30°$ C., preferably at $0°$ C., in the course of five minutes to one hour, preferably in the course of 20 minutes.

After splitting off the protective group, the acid of the formula (VIII) can be isolated. Advantageously, however, the acid is not isolated but is reacted directly and without purification to give compounds of the formula (VI). For this, the solution of (VIII) formed in the reaction (VII→VIII) is concentrated under mild conditions in vacuo. The crude acid which remains is taken up in an organic solvent, preferably in tetrahydrofuran, and reacted with 2–20 equivalents, preferably 5–10 equivalents, of a tertiary amine of the formula $R^5$
|
$N-R^6$
|
$R^7$ in which
$R^5$, $R^6$ and $R^7$ have the abovementioned meaning, to give compounds of the formula (VI). The reaction is carried out at temperatures between $-20°$ C. and $40°$ C., preferably at $25°$ C., in the course of 10 minutes to 2 hours, preferably in the course of 30 minutes. When the reaction has ended, the product can be precipitated by addition of diethyl ether. The crude product thus obtained can be purified on a resin, such as Diaion HP 20 or XAD 7. It is also advantageously possible for the crude product to be further reacted directly to give compounds of the formula (III).

Alternatively, the compounds of the formula (VI) can be prepared from acids of the formula (IX) in which $R^{16}$

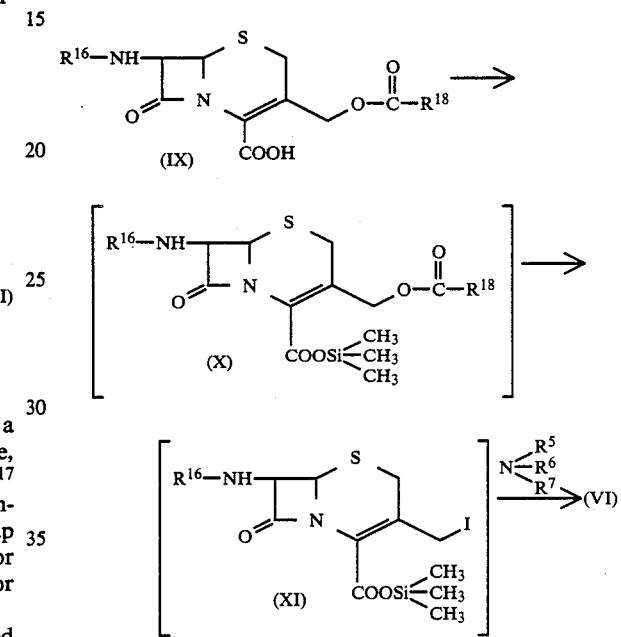

has the abovementioned meaning and $R^{18}$ represents an optionally substituted alkyl or aryl radical, such as methyl, ethyl, propyl, chloromethyl, dichloromethyl, trichloromethyl, trifluoromethyl or phenyl. $R^{18}$ especially preferably represents a methyl group.

The starting compounds of the formula (IX) are suspended in a suitable organic solvent and dissolved by silylation to give the silyl ester X. Particularly suitable organic solvents are chloroform, methylene chloride and dichloroethane. The silylation is carried out with a customary silylating agent, such as trimethylchlorosilane (TMCS), hexamethyldisilazane (HMDS), N,O-bis(trimethylsilyl)-acetamide (BSA), N,O-bis(trimethylsilyl)-trifluoroacetamide (BSTFA), N-methyl-N-trimethylsilylacetamide (MSA), N-methyl-N-trimethylsilyl-trifluoroacetamide (MSTFA), 1,3-bis(trimethylsilyl)urea or trimethylsilyl trifluoromethanesulphonate. Several silylating agents can also be used here as a mixture.

The silylation is carried out at $-30°$ C. to $70°$ C., preferably at $-10°$ C. to $+10°$ C., in the course of five minutes to 30 minutes. An excess of up to 10-fold of the silylating agent, preferably a two- to five-fold excess, is advantageously employed.

The resulting solution of the trimethylsilyl ester of the formula (X) is reacted with one to 10 equivalents, preferably with three to four equivalents, of a trialkylsilyliodide, particularly preferably trimethylsilyl iodide, at −40° C. to +30° C., preferably at −10° C. to +10° C., in the course of 15 minutes to two hours, preferably in the course of 30 minutes to one hour, to give compounds of the formula (XI).

The compounds of the formula (XI) are advantageously not isolated, but are reacted directly, without purification, with amines $$N \underset{R^7}{\overset{R^5}{\underset{R^6}{\rightleftharpoons}}}$$

to give compounds of the formula (VI).

The substances of the general formula (II) used as starting compounds are new and the invention likewise relates to them.

The compounds of the formula (IIa) in which $R^1$ represents alkyl or trifluoromethyl and $R^2$ has the meaning given are obtained by a process in which compounds of the formula (XII)

$$\underset{R^1\quad O}{Hal\text{-}CH\text{-}C\text{-}CH_2\text{-}COOR^{17}} \quad (XII)$$

in which

Hal represents chlorine or bromine, $R^{17}$ represents branched or straight-chain, optionally substituted $C_1$–$C_4$-alkyl, preferably methyl, ethyl or tert.-butyl, or represents trimethylsilylethyl and $R^1$ has the meaning given, are reacted in a first step with aldehydes of the formula (XIII)

$$R^2\text{—CHO} \quad (XIII)$$

in which $R^2$ has the meaning given, if appropriate in inert organic solvents, such as alcohols, for example methanol, ethanol or propanol, if appropriate in the presence of piperidine and glacial acetic acid, to give the ylidene compounds of the general formula (XIV)

$$\underset{R^1\ \ O\ \ \underset{R^2}{CH}}{Hal\text{-}CH\text{-}C\text{-}C\text{-}COOR^{17}} \quad (XIV)$$

in which $R^1$, $R^2$ and $R^{17}$ have the meaning given, and the compounds (XIV) are reacted in a second step with acetylthiourea in water and/or inert organic solvents, such as alcohols, for example methanol, ethanol or propanol, or formamides, such as, for example, dimethylformamide, in particular in mixtures of water and dimethylformamide, to give acetylaminothiazoles of the formula (XV)

$$H_3C\text{-}\underset{O}{\overset{}{C}}\text{-}NH\text{-}\underset{N}{\overset{S}{\underset{}{\rightleftharpoons}}}\underset{R^2}{\overset{R^1}{\underset{COOR^{17}}{}}} \quad (XV)$$

in which $R^1$, $R^2$ and $R^{17}$ have the meaning given, and the esters of the formula (XV) are then hydrolyzed with the aid of aqueous bases, such as, for example, potassium hydroxide or sodium hydroxide, if appropriate in the presence of alcohols, such as methanol or ethanol, to give acids of the formula (IIa). The process is carried out by a procedure analogous to the process described in U.S. Pat. No. 4,416,880.

The compounds (IIb) in which $R^1$ represents halogen, alkoxy or alkylthio and $R^2$ has the meaning already given, are obtained by a process in which compound's of the formula (XV) in which $R^1$ is H are halogenated with halogenating agents, such as, for example, bromine, chlorine, N-bromosuccinimide, N-chlorosuccinimide, sulphonyl chloride or sulphuryl bromide, in particular sulphuryl bromide or sulphuryl chloride, if appropriate in inert organic solvents, such as halogenohydrocarbons, such as methylene chloride, chloroform, carbon tetrachloride, 1,2-dichloroethane, 1,1,2-trichloroethane or dichloroethylene, or hydrocarbons, such as benzene, toluene or xylene, in particular in halogenohydrocarbons, if appropriate E/Z mixtures (in respect of the double bond) are separated by customary processes, for example by chromatography or crystallization, and, if appropriate, chlorine or bromine is replaced by fluorine, alkoxy or alkylthio by customary methods.

The procedure for this process is described in principle in DE-OS (German Published Specification) Nos. 2,758,000 or 2,758,001 and EP-OS (European Published Specification) Nos. 34,760 and 55,456. The compounds (IIb) can be prepared by a process analogous to the processes described therein.

The aldehydes of the formula (XII) used as starting compounds are known or can be prepared by methods which are known from the literature (E. Mosettig, Organic Reactions Volume III, 218 et seq. (1954)).

The halogen compounds of the formula (XIV) used as starting compounds are known or can be prepared by known methods.

The compounds according to the invention exhibit a broad antibacterial spectrum against Gram-positive and Gram-negative germs, in particular against Enterobacteriaceae; above all against those which are resistant to various antibiotics, such as, for example, penicillins, cephalosporins, aminoglycosides, sulphonamides and tetracyclines, coupled with a low toxicity.

These useful properties enable them to be used as chemotherapeutic active compounds in medicine and as substances for preserving inorganic and organic materials, in particular all types of organic materials, for example polymers, lubricants, paints, fibers, leather, paper and wood, and foodstuffs and water.

The compounds according to the invention are active against a very broad spectrum of microorganisms. With the aid of these compounds, Gram-negative and Gram-positive bacteria and bacteria-like microorganisms can be combated and the diseases caused by these pathogens can be prevented, alleviated and/or cured.

The compounds according to the invention are particularly active against bacteria and bacteria-like microorganisms. They are therefore particularly suitable in human and veterinary medicine for the prophylaxis and chemotherapy of local and systemic infections caused by these pathogens.

For example, local and/or systemic diseases which are caused by the following pathogens or by mixtures of the following pathogens can be treated and/or prevented: Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoeae*) and Gram-negative rod-shaped bacilli, such as Enterobacteriaceae, for example *Escherichia coli*, Haemophilus influenzae, Citrobacter (*Citrob. freundii* and *Citrob. divernis*), Salmonella and Shigella; and furthermore Klebsiellae (Klebs. pneumoniae and Klebs. oxytoca), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the genus Acinetobacter. The antibacterial spectrum moreover includes the genus Pseudomonas (*Ps. aeruginosa* and *Ps. maltophilia*) and strictly anaerobic bacteria, such as, for example, *Bacteroides fragilis*, representatives of the genus Peptococcus, Peptostreptococcus and the genus Clostridium; and furthermore Mycoplasma (*M. pneumoniae, M. hominis* and *M. urealyticum*) as well as mycobacteria, for example *Mycobacterium tuberculosis*.

The above list of pathogens is to be interpreted merely by way of example and in no as limiting. Examples which may be mentioned of diseases which can be caused by the pathogens mentioned or mixed infections and which can be prevented, alleviated or cured by the compounds according to the invention are: infectious diseases in humans, such as, for example, otitis, pharyngitis, pneumonia, peritonitis, pyelonephritis, cystitis, endocarditis, systemic infections, bronchitis (acute and chronic), septic infections, diseases of the upper respiratory tract, diffuse panbronchiolitis, pulmonary emphysema, dysentery, enteritis, hepatic abscesses, urethritis, prostatitis, epididymitis, gastrointestinal infections, bone and joint infections, cystic fibrosis, skin infections, postoperative wound infections, abscesses, phlegmon, wound infections, infected burns, burn wounds, infections in the oral region, infections following dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhoid fever, meningitis and infections of the nervous system, salpingitis, endometritis, genital infections, pelveoperitonitis and eye infections.

As well as on humans, bacterial infections can also be treated on other species. Examples which may be mentioned are: pigs: coli diarrhoea, enterotoxaemia, sepsis, dysentery, salmonellosis, metritis-mastitisagalactiae syndrome and mastitis; ruminants (cattle, sheep, goats): diarrhoea, sepsis, bronchopneumonia, salmonellosis, pasteurellosis, mycoplasmosis and genital infections; horses: bronchopneumonia, jointill, puerperal and post-puerperal infections and salmonellosis; dogs and cats: bronchopneumonia, diarrhoea, dermatitis, otitis, urinary tract infections and prostatitis; poultry (chicken, turkeys, quail, pigeons, ornamental birds and others): mycoplasmosis, *E. coli* infections, chronic respiratory tract infections, salmonellosis, pasteurellosis and psittacosis.

Bacterial diseases can also be treated in the breeding and rearing of stock and ornamental fish, the antibacterial spectrum being extended beyond the abovementioned pathogens to other pathogens, such as, for example, Pasteurella, Brucella, Campylobacter, Listeria, Erysipelothrix, Corynebacteria, Borellia, Treponema, Nocardia, Rickettsia and Yersinia.

The present invention includes pharmaceutical formulations which contain one or more compound according to the invention, in addition to non-toxic, inert pharmaceutically suitable excipients, or which consist of one or more active compounds according to the invention, and processes for the preparation of these formulations.

The present invention also includes pharmaceutical formulations in dosage units. This means that the formulations are in the form of individual parts, for example tablets, dragees, capsules, pills, suppositories and ampules, the active compound content of which correspond to a fraction or a multiple of an individual dose. The dosage units can contain, for example, one, two, three or four individual doses or half, one-third or one-quarter of an individual dose. An individual dose preferably contains the amount of active compound which is given in one administration and which usually corresponds to a whole, one-half, one-third or one-quarter of a daily dose.

Non-toxic, inert pharmaceutically suitable excipients are to be understood as solid, semi-solid or liquid diluents, fillers and formulation auxiliaries of all types.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silicic acid, (b) binders, for example carboxymethylcellulose, alginates, gelatin and polyvinylpyrrolidone, (c) humectants, for example glycerol, (d) disintegrating agents, for example agaragar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only or preferentially in a particular part of the intestinal tract, optionally in a delayed manner, examples of embedding compositions which can be used being polymeric substances and waxes.

The active compound or compounds can also be in microencapsulated form, if appropriate with one or more of the abovementioned excipients.

Suppositories can be contain, in addition to the active compound or compounds, the customary water-soluble or water-insoluble excipients, for example polyethylene glycols, fats, for example cacao fat, and higher esters (for example C₁₄-alcohol with C₁₆-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Powders and sprays can contain, in addition to the active compound or compounds, the customary excipients, for example lactose, talc, silicic acid, aluminum hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cotton seed oil, groundnut oil, corn germ oil, olive oil, castor oil and sesame oil, glycerol, methylidinoglycerol, tetrahydrofuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propylene glycol, suspending agents, for example ethoxylated isostearyl alcohols, polyoxyethylene sorbitol and sorbitan esters, microcrystalline cellulose, aluminum metahydroxide, bentonite, agaragar and tragacanth, or mixtures of these substances.

The formulation forms mentioned can also contain colouring agents, preservatives and additives which improve the smell and taste, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds in addition to the compounds according to the invention.

The abovementioned pharmaceutical formulations are prepared in the customary manner by known methods, for example by mixing the active compound or compounds with the excipient or excipients.

The formulations mentioned can be used on humans and animals either orally, rectally, parenterally (intravenously, intramuscularly or subcutaneously), intracisternally, intravaginally, intraperitoneally and locally (powder, ointment and drops) and for the therapy of infections in hollow cavities and body cavities. Possible suitable formulations are injection solutions, solutions and suspensions for oral therapy, gels, infusion formulations, emulsions, ointments or drops. Opthalmological and dermatological formulations, silver salts and other salts, ear drops, eye ointments, powders or solutions can be used for local therapy. On animals, intake can also be via the feed or drinking water in suitable formulations. It is furthermore possible to use gels, powders, dusts, tablets, sustained-release tablets, premixes, concentrates, granules, pellets, boli, capsules, aerosols, sprays and inhalates on humans and animals. The compounds according to the invention can furthermore be incorporated into other carrier materials, such as, for example, plastics (chains of plastic for local therapy), collagen or bone cement.

The new compounds can be administered in the customary concentrations and formulations together with the feed or with feed formulations or with the drinking water. Infection by Gram-negative or Gram-positive bacteria can thereby be prevented, alleviated and/or cured, and a promotion in growth and an improvement in feed utilization can thereby be achieved.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably contains the active compound or compounds according to the invention in amounts of about 1 to about 80, in particular 3 to 30, mg/kg of body weight. However, it may be necessary to deviate from the dosages mentioned, and in particular to do so as a function of the nature and body weight of the subject to be treated, the nature and severity of the disease, the nature of the formulation and of the administration of the medicament and the period or interval within which administration takes place.

Thus it can in some cases be sufficient to manage with less than the abovementioned amount of active compound, whilst in other cases the abovementioned amount of active compound must be exceeded. The particular optimum dosage and mode of administration of the active compounds required can easily be specified by any expert on the basis of his expert knowledge.

The compounds according to the invention can be combined with other antimicrobial active compounds and lactamase inhibitors, for example with penicillins which are particularly penicillinase-resistant and clavulanic acid, for the purpose of extending the action spectrum and in order to achieve an increase in action, in particular in the case of bacteria which form β-lactamase. Such a combination would be, for example, that with oxacillin or dicloxacillin.

The compounds according to the invention can also be combined with aminoglycoside antibiotics, such as, for example, gentamicin, sisomicin, kanamycin, amikacin or tobramycin.

PREPARATION EXAMPLES

EXAMPLE 1

Ethyl 4-bromo-3-oxovalerate

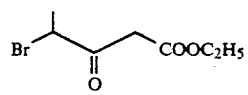

277 g of bromine are added dropwise to a solution of 250 g of ethyl 3-oxovalerate and 0.5 g of p-toluenesulphonic acid in 55 ml of methyl chloride at room temperature, while stirring. The mixture is subsequently stirred at 30° C. for one hour, ice-water is added and the organic phase is separated off. The aqueous phase is extracted once more with methylene chloride and the combined organic phases are then dried over magnesium sulphate and evaporated. The product is further processed in the crude form.

Yield: 350 g=90% of theory.

EXAMPLE 2

Ethyl 2-ethylidene-4-bromo-3-oxovalerate

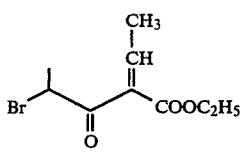

A solution of 100 g (0.45 mol) of ethyl 4-bromo-3-oxovalerate in 100 ml of absolute methylene chloride is cooled to −20° C. under nitrogen, and 50 g (1.12 mol) of acetaldehyde are added. 1 g of piperidine, dissolved in 10 ml of methylene chloride, is then added dropwise at −20° C.

The mixture is subsequently stirred at −20° C. for 30 minutes and then at −5° C. for 2.5 hours, and 100 ml of ice-cold 2N hydrochloric acid are then added. The organic phase is separated off, the aqueous solution is washed once more with methylene chloride and the combined organic phases dried and evaporated. A crude product which, according to the gas chromatogram, is a 2.5:1 isomer mixture with a purity of 88% and which can be further processed in the crude form is obtained.

Yield: 95 g=85% of theory.

EXAMPLE 3

Ethyl Z-2-(2-acetamido-5-methylthiazol-4-yl)but-2-enoate

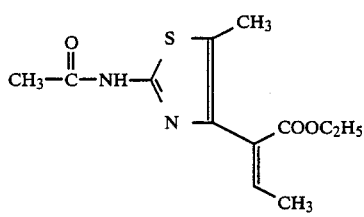

24.9 g (theoretically 0.1 mol) of ethyl 2-ethylidene-4-bromo-3-oxovalerate (crude product) and 8.2 g (0.07 mol) of acetylthiourea are dissolved in a mixture of 50 ml of water and 90 ml of dimethylformamide. The solution is warmed at 85° C. for one hour, while stirring, and is then cooled in an ice-bath for one hour, and the product which has precipitated is filtered off with suction. The product is washed once with water/dimethylformamide=4/1, once with water/dimethylformamide=9/1 and once with water and dried.

Yield: 10.7 g=39.3% of theory; melting point: 166° C.

According to high-performance liquid chromatography (column: RP8 10µ 250/4; mobile phase: buffer pH 7/acetonitrile 40/60; 2 ml/min), the product is 94% isomerically pure, and it is allocated the Z configuration by NMR comparison with known products and on the basis of the antibacterial action of the subsequent products.

$^1$H-NMR(DMSO-d$_6$): δ(ppm)=6.32 [1] q, J=8 Hz, 4.20 [2] q, a=7 Hz, 2.24 [3] s, 2.12 [3] s, 1.97 [3] d, J=8 Hz, 1.23 [3] t, J=7 Hz.

EXAMPLE 4

Z-2-(2-amino-5-methylthiazol-4-yl)but-2-enoic acid

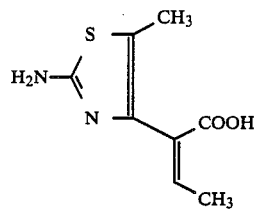

27 g (0.1 mol) of ethyl Z-2-(2-acetamino-5-methylthiazol-4-yl)but-2-enoate are added all at once to a solution, stirred at 85° C., of 29 g (0.5 mol) of potassium hydroxide in 198 ml of water. The mixture is subsequently stirred at 80° C. for two hours and then cooled with an ice-bath and the pH is brought to 3.0 with concentrated hydrochloric acid, while cooling with ice. The aqueous solution is decanted from the oily residue, concentrated to one-fifth of its volume and decanted again. The combined residues are crystallized with acetone. Yield: 7.8 g=39.1% of theory.

High-performance liquid chromatography (column: NH$_2$ 5µ, 250/4, mobile phase: methanol/water/glacial acetic acid 100/10/6, 1.5 ml/minute): 1.39 minutes, purity 96%

$^1$H-NMR(DMSO-d$_6$): δ(ppm)=6.80 [2] bs, 6.19 [1] q, J=8 Hz, 2.12 [3] s, 1.92 [3] d, J=8 Hz.

EXAMPLE 5

Ethyl E/Z-2-(2-acetamido-5-chlorothiazol-4-yl)but-2-enoate

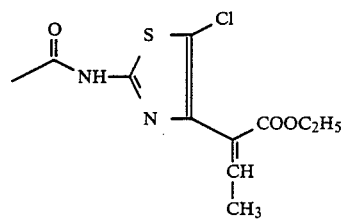

50.8 g (0.2 mol) of ethyl Z-2-(2-acetamidothiazol-4-yl)buten-2-oate are suspended in a mixture of 1.2 l of chloroform and 140 ml of glacial acetic acid at −40° C. A solution of 31 g (0.44 mol) of chlorine in carbon tetrachloride is added dropwise, while stirring, and the mixture is then allowed to come to room temperature and is evaporated. Crystallization from ether/ligroin gives 52 g=72% of theory, melting point: 140°–142° C. A 1:1 diastereomer mixture of ethyl 2-(2-acetamido-5-chlorothiazol-4-yl)-2,3-dichlorobutanoate is formed.

$^1$H-NMR(CDCl$_3$):

Isomer A: δ(ppm)=7.56 [1] bs, 5.22 [1] q, J=8 Hz, 4.33 [2] q, J=7 Hz, 2.29 [3] s, 1.78 [3] d, J=8 Hz, 1.30 [3] t, J=7 Hz.

Isomer B: δ(ppm)=7.64 [1] bs, 5.10 [1] q, J=8 Hz, 4.32 [2] q, J=7 Hz, 2.31 [3] s, 1.70 [3] d, J=8 Hz, 1.31 [3] t, J=7 Hz.

MS: 358 (M+), 316 (M+ −CH$_2$=C=O).

Calc.: C 36.7 H 3.6 N 7.8 S 8.9 Cl 29.6. Fnd.: C 36.8 H 3.7 N 8.2 S 8.8 Cl 28.5.

A spatula-tip of zinc chloride is first introduced into a solution of 5 g (13.9 mol) of this product in 20 ml of boiling methanol, and 1 g (15.3 mol) of zinc dust are then introduced in portions in the course of 30 minutes. The mixture is subsequently boiled for a further hour and then cooled and evaporated. The residue is taken up in ice-water/ethyl acetate and the solution is brought to pH 2 with 6N hydrochloric acid. After the water has been separated off, the organic phase is extracted once more with 1N hydrochloric acid, once with water, three times with saturated sodium bicarbonate solution and once with water and is dried and evaporated. Chromatography of the crude product on silica gel (mobile phase: toluene/acetone 3/1) gives 600 mg of the pure Z isomer, melting point 186°-7° (ether) and 500 mg of E/Z mixture. Total yield: 24.9% of theory.

$^1$H-NMR(CDCl$_3$): Z-Isomer: δ(ppm)=10.27 [1] bs, 6.58 [1] q, J=8 Hz, 4.23 [2] q, J=7 Hz, 2.13 [3] s, 2.06 [3] d, J=8 Hz, 1.22 [3] t, J=7 Hz.

E-Isomer: δ(ppm)=10.50 [1] bs, 7.26 [1] q, J=8 Hz, 4.18 [2] q, J=7 Hz, 2.11 [3] s, 1.72 [3] d, J=8 Hz, 1.20 [3] t, J=7 Hz.

EXAMPLE 6

Ethyl Z-2-(5-chloro-2bis-tert.-butoxycarbonyl-amino-thiazol-4-yl)-but-2-enoate

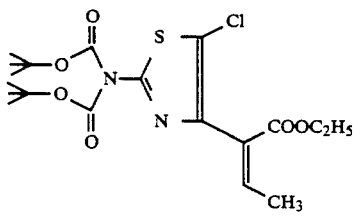

64.2 g (0.29 mol) of di-tert.-butyl dicarbonate are added dropwise to a solution of 25.5 g (0.09 mol) of ethyl Z-2-(2-acetamido-5-chlorothiazol-4-yl)but-2-enoate in 110 ml of pyridine at room temperature, while stirring. The mixture is stirred overnight at room temperature and warmed at 50° C. for one hour, and the conversion is checked by thin-layer chromatography. If necessary, a further 10.7 g (0.05 mol) of di-tert.-butyl dicarbonate are added and the solution is stirred for a further night. The pyridine is then stripped off, the oil which remains is dissolved in ethyl acetate and the solution is washed three times with 6N hydrochloric acid and once with water. Drying and evaporation gives a mobile oil which, according to NMR, consists of 80% of the product and 20% of di-tert.-butyl dicarbonate. It can be employed in the next stage in crude form. Yield: 34 g.

$^1$H-NMR(CDCl$_3$): δ(ppm)=6.62 [1] q, J=8 Hz, 4.25 [1] q, J=7 Hz, 2.02 [3] d, J=8 Hz, 1.53 [18] s, 1.27 [3] t, J=7 Hz.

EXAMPLE 7

E/Z-2-(5-chloro-2-tert.-butoxycarbonylaminothiazol-4-yl)but-2-enoic acid

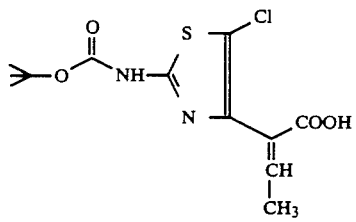

25 g (theoretically 0.056 mol) of ethyl Z-2-(5-chloro-2-bis-tert.-butyloxycarbonylaminothiazol-4-yl)but-2-enoate, dissolved in 200 ml of ethanol, are added to a solution of 22.8 g (0.56 mol) of sodium hydroxide in 200 ml of water at room temperature. The mixture is stirred overnight at room temperature, the ethanol is stripped off and the aqueous solution is extracted three times with ethyl acetate. Ethyl acetate is added to the aqueous phase and the mixture is brought to pH 1 with 6N hydrochloric acid and extracted a total of three times with ethyl acetate. Drying and evaporation of this last ethyl acetate phase gives a crude product from which 3.8 g of the E isomer can be crystallized with carbon tetrachloride. The mother liquor is evaporated and, according to high-performance LC (column: NH$_2$, 5μ, 125/4, mobile phase: methanol/water/glacial acetic acid 100/10/3, 2 ml/minute), it contains 41% of E isomer (retention time 2.4 minutes) and 22% of Z isomer (retention time 6.0 minutes). This mixture is dissolved in methanol and separated on Lewatit MP 62 with the addition of increasing amounts of acid (1. methanol, 2. 0.5% strength glacial acetic acid, 3. 1% strength glacial acetic acid, 4. 5% strength concentrated hydrochloric acid, 5. 10% strength concentrated hydrochloric acid). The E isomer is first eluted together with all the impurities, and finally the pure Z isomer is eluted.

E ISOMER

Yield: 3.8 g=26.6% of theory, melting point: 190° C. (CCl$_4$).

$^1$H-NMR(CDCl$_3$): δ(ppm)=8.72 [1] bs, 7.26 [1] q, J=8 Hz, 1.73 [3] d, J=8 Hz, 1.50 [9] s.

Z-ISOMER

Yield: 0.9 g=6.3% of theory, melting point 190° (CCl$_4$)

$^1$H-NMR(CDCl$_3$): δ(ppm)=10.9 [1] bs, 6,63 [1] q, J=8 Hz, 2,16 [3] d, J=8 Hz, 1,56 [9] s.

EXAMPLE 8

Z-2-(2-amino-5-chlorothiazol-4-yl)but-2-enoic acid

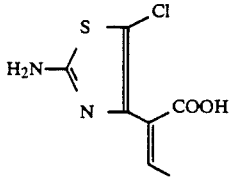

0.7 g of Z-2-(5-chloro-2-tert.-butoxycarbonylamino-thiazol-4-yl)but-2-enoic acid are dissolved in 5 ml of trifluoroacetic acid at 0° C. under nitrogen. The mixture is stirred at room temperature for one hour and evaporated in the cold and the residue is suspended in ethyl acetate. The pH is brought to 3.5 with saturated sodium bicarbonate solution, while stirring, the product first dissolving and then precipitating again. The product is filtered off with suction, washed with ethyl acetate and dried.

Yield: 0.3 g=62.5% of theory; melting point: sinters from 130° C.

$^1$H-NMR(DMSO-d$_6$): δ(ppm)=12.73 [1] bs, 7.18 [2] s, 6.40 [1] q, J=8 Hz, 1.92 [3] d, J=8 Hz.

EXAMPLE 9

Tert.-butyl 4-chloro-2-ethylidene-3-oxobutyrate

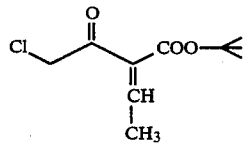

1.5 ml of piperidine are added dropwise to a stirred mixture of 212 g (1.1 mol) of tert.-butyl 4-chloro-3-oxobutyrate and 97 g (2.2 mol) of acetaldehyde at −20° C. under nitrogen. The mixture is subsequently stirred at −20° C. for six hours and is then worked up analogously to Example 2. Crude yield: 210 g, content according to gas chromatography: 6% of starting material, 52+37% of an isomer mixture of the product. The product is further processed in the crude form.

$^1$H-NMR(CDCl$_3$);

Isomer A: δ(ppm)=7.11 [1] q, J=8 Hz, 4,33 [2] s, 1.91 [3] d, J=8 Hz, 1.49 [9] s.

Isomer B: δ(ppm)=7.08 [1] q, J=8 Hz, 4.40 [2] s, 2.08 [3] d, J=8 Hz, 1.54 [9] s.

EXAMPLE 10

Tert.-butyl Z-2-(2-acetamidothiazol-4-yl)but-2-enoate

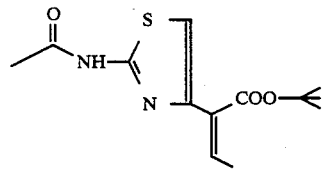

The crude product of a 2.2 mol batch of tert.-butyl 4-chloro-2-ethylidene-3-oxobutyrate, dissolved in 100 ml of dimethylformamide, is added to a solution, warmed to 85° C., of 236 g (2 mol) of acetylthiourea in a mixture of 360 ml of water and 720 ml of dimethylformamide. The mixture is stirred at 85° C. for two hours and concentrated, the residue is taken up in ethyl acetate and the solution is extracted three times with water. After drying and concentrating, by-products are precipitated with ether.

The combined mother liquors are evaporated. Some of the desired product (24.8 g) can be crystallized out of the residue with ligroin/ether, and the mother liquor is chromatographed over silica gel (mobile phase: 1. toluene, 2. toluene/acetone 9/1). The fractions containing the product are likewise crystallized with ligroin/ether. Yield: 109 g=17.5% of theory, melting point: 143°-45° C.

$^1$H-NMR(DMSO-d$_6$): δ(ppm)=12.2 [1] bs, 6.90 [1] s, 6.70 [1] q, J=8 Hz, 2.20 [3] s, 1.87 [3] d, J=8 Hz, 1.54 [9] s.

EXAMPLE 11

Tert.-butyl Z-2-(2-acetamido-5-chlorothiazol-4-yl)but-2-enoate

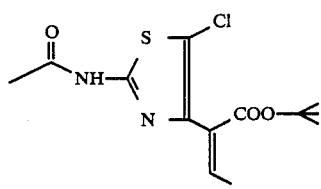

78 g (0.28 mol) of tert.-butyl Z-2-(2-acetamidothiazol-4-yl)but-2-enoate are suspended in a mixture of 2 l of carbon tetrachloride and 15 ml of glacial acetic acid at 0° C. 43 g (0.32 mol) of sulphuryl chloride, dissolved in 600 ml of carbon tetrachloride, are added dropwise in the course of five hours, while stirring. The solution is extracted once with saturated sodium bicarbonate solution and once with water, dried and concentrated to about 200 ml. The product which has precipitated is filtered off with suction and washed with ether (53.4 g). The mother liquor is evaporated completely and a second fraction of the product (6 g) is obtained by crystallization of the residue with ether/ligroin. Yield: 59.4 g=67.8% of theory.

$^1$H-NMR(CDCl$_3$): δ(ppm)=10.21 [1] bs, 6.53 [1] q, J=8 Hz, 2.18 [3] s, 2.07 [3] d, J=8 Hz, 1.49 [9] s.

EXAMPLE 12

Tert.-butyl Z-2-(5-chloro-2-tert.-butoxycarbonylaminothiazol-4-yl)but-2-enoate and

EXAMPLE 13

Tert.-butyl Z-2-(5-chloro-2-bis-tert.-butoxycarbonylaminothiazol-4-yl)but-2-enoate

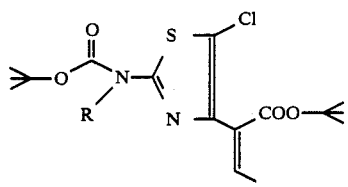

| Exmp. | R |
|---|---|
| 12 | H |
| 13 | (H$_3$C)$_3$COCO |

A solution of 59 g (0.19 mol) of tert.-butyl Z-2-(2-acetamido-5-chlorothiazol-4-yl)but-2-enoate and 122 g (0.56 mol) of di-tert.-butyl dicarbonate in 500 ml of pyridine is stirred at room temperature for three days and then concentrated. The residue is taken up in ethyl acetate and the mixture is extracted three times with 20% strength hydrochloric acid and once with saturated sodium chloride solution. After drying over sodium sulphate and evaporation, the residue is chromatographed on 3 kg of silica gel (mobile phase: 1. toluene 2. toluene/ethyl acetate 9/1). First Example 13 and then 12 are eluted.

EXAMPLE 13

Yield: 25 g of an oil (=28.2% of theory), still contains residues of [(H₃C)₃C-OCO]₂O ¹H-NMR(CDCl₃) δ(ppm)=6.60 [1] q, J=8 Hz, 2.57 [3] d, J=8 Hz, 1.55 [18] s, 1.54 [9] s.

EXAMPLE 12

Yield: 40 g of solid foam=57.3% of theory

¹H-NMR(CDCl₃): δ(ppm)=9.08 [1] bs, 6.54 [1] q, J=8 Hz, 2.07 [3] d, J=8 Hz, 1.52 [18] s.

EXAMPLE 14

Z-2-(2-amino-5-chlorothiazol-4-yl)but-2-enoic acid

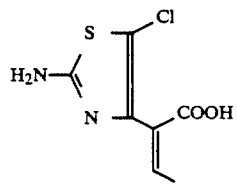

40 g of Z-2-(5-chloro-2-tert.-butoxycarbonylaminothiazol-4-yl)but-2-enoic acid are dissolved in 200 ml of trifluoroacetic acid at 0° C. After the solution has been left to stand at room temperature for two hours, it is evaporated in the cold, the residue is crystallized with water and the crystals are filtered off with suction and dried.

Yield: 30 g of the trifluoroacetic acid salt of the product=87.6% of theory

¹H-NMR(DMSO-d₆): δ(ppm)=6.52 [1] q, J=8 Hz, 2.00 [3] d, J=8 Hz.

This product is converted into the free base analogously to Example 8, the analytical data of the free base corresponding to those given in Example 8. Yield: 18.8 g=80.5% of theory.

EXAMPLE 15

Z-7-[2-(2-amino-5-methylthiazol-4-yl)but-2-enoyl-]amino-3-pyridinium-methyl-cephem-4-carboxylate

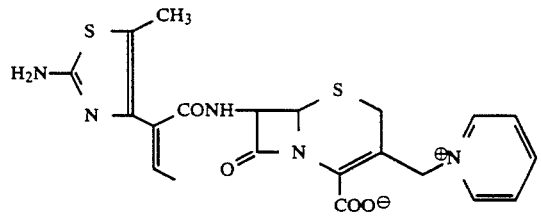

A solution of 1.2 g of Z-2-(2-amino-5-methylthiazol-4-yl)but-2-enoic acid (6 mmol) and 1.8 ml of triethylamine (12.8 mmol) in 7.2 ml of dimethylformamide is cooled to −50° C. under nitrogen, and 0.5 ml (6.3 mmol) of methanesulphonyl chloride are added. The mixture is subsequently stirred at −50° C. for two hours. A solution of 1.7 g (4.9 mmol) of 7-amino-3-pyridiniummethyl-3-cephem-4-carboxylate hydrochloride hydrate and 2.3 ml (16 mmol) of triethylamine in 2.3 ml of water is added to the cold solution at −50° C., the cooling bath is removed, the mixture is subsequently stirred for 10 minutes and the solution is then poured onto 70 ml of acetone. The product which has precipitated is filtered off with suction and dried. Chromatography on LOBAR C (RP 8, mobile phase: water-/acetonitrile 8/2) gives 0.3 g of pure product=10.5% of theory.

¹H-NMR(DMSO-d₆): δ(ppm)=9.49 [2] d, J=6 Hz, 9.10 [1] d, J=7 Hz, 8.62 [1] bt, J=7 Hz, 8.20 [2] bt, J=7 Hz, 6.75 [2] bs, 6.12 [1] q, J=8 Hz, 5.72 [1] dd, J=7 Hz, J=5 Hz, 5.68 [1] d, J=13 Hz, 5.13 [1] d, J=13 Hz, 5.10 [1] d, J=5 Hz, 3.54 [1] d, J=18 Hz, 3.06 [1] d, J=18 Hz, 2.08 [3] s, 1.80 [3] d, J=8 Hz.

EXAMPLE 16

Sodium Z-7-[2-(2-amino-5-chlorothiazol-4-yl)but-2-enoyl-]amino-3-acetoxymethyl-3-cephem-4-carboxylate

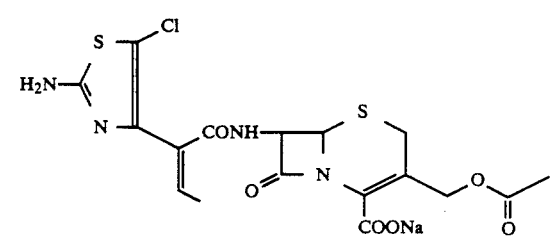

1.4 g of Z-2-(2-amino-5-chlorothiazol-4-yl)but-2-enoic acid are activated in accordance with the instructions of Example 15 and coupled with 2.09 g of 7-ACS with the addition of 1.9 g of triethylamine. The crude product is purified over Diaion HP 20.

Yield: 1 g=32% of theory

¹H-NMR(DMSO-d₆): δ(ppm)=9.19 [1] d, J=8 Hz, 7.29 [2] bs, 6.43 [1] q, J=8 Hz, 5.64 [1] dd, J=8 Hz, J=5 Hz, 5.07 [1] d, J=5 Hz, 5.03 [1] d, J=13 Hz, 4.79 [1] d, J=13 Hz, 3.51 [1] d, J=18 Hz, 3.24 [1] d, J=18 Hz, 2.03 [3] s, 1.89 [1] d, J=8 Hz.

EXAMPLE 17

Z-7-[2-(2-amino-5-chlorothiazol-4-yl)but-2-enoyl-]amino-3-pyridinium-methyl-3-cephem-4-carboxylate

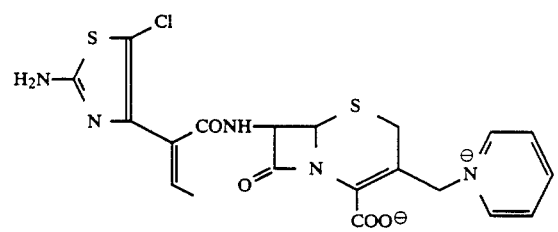

5.6 g (25.6 mmol) of Z-2-(2-amino-5-chlorothiazol-4-yl)but-2-enoic acid are activated in accordance with the instructions of Example 15 and then coupled with a solution of 6.8 g (19.7 mmol) of 7-amino-3-pyridiniummethyl-3-cephem-4-carboxylate hydrochloride hydrate and 6.6 ml (47.4 mmol) of triethylamine in 20 ml of water. Purification of the crude product, precipitated from acetone, on Diaion HP 20 gives 6.5 g=51.6% of theory.

¹H-NMR(DMSO-d₆): δ(ppm)=9.55 [2] d, J=6 Hz, 9.19 [1] d, J=7 Hz, 8.64 [1] bt, J=7 Hz, 8.20 [2] bt, J=6 Hz, 7.23 [2] bs, 6.36 [1] q, J=8 Hz, 5.71 [1] d, J=13 Hz, 5.69 [1] dd, J=7 Hz, J=5 Hz, 5.14 [1] d, J=13 Hz, 5.10 [1] d, J=5 Hz, 3.55 [1] d, J=18 Hz, 3.05 [1] d, J=18 Hz, 1.80 [3] d, J=8 Hz.

cal. x 1.5 H₂O=C 46.3 H 4.1 N 13.5 S 12.3 Cl 6.8. fnd.=C 46.3 H 4.0 N 13.4 S 11.6 Cl 7.1.

EXAMPLE 18

Z-7-[2-(2-amino-5-chlorothiazol-4-yl)but-2-enoyl-]amino-3-(4-amino-carbonyl-1-methylpiperazinium)-methyl-3-cephem-4-carboxylate

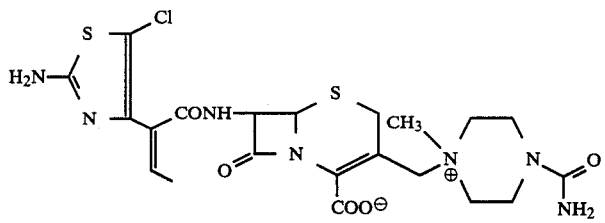

(a) 7-amino-3-(4-aminocarbonyl-1-methylpiperazinium)-methyl-3-cephem-4-carboxylate 9.36 g (24 mmol) of 3-acetoxymethyl-7-β-phenylacetamido-3-cephem-4-carboxylic acid are suspended in 100 ml of absolute methylene chloride at room temperature under nitrogen and are dissolved by addition of 15.2 ml (72 mmol) of N-methyl-N-trimethyl-silyltrifluoroacetamide (MSTFA). After cooling to 0° C., 14 ml (96 mmol) of trimethylsilyl iodide are added and the reaction solution is stirred at 0° C. for one hour. 34 g of 1-aminocarbonyl-4-methylpiperazine are dissolved, in 150 ml of dimethylformamide, are then added and the solution is subsequently stirred for 30 minutes. 4.8 ml of $H_2O$ are then added and, after a further five minutes, the mixture is poured onto 400 ml of ether. The ether is decanted off from the oily residue. 5 g of the product are dissolved in 100 ml of $H_2O$ and the pH is brought to 7.8 with 4N triethylamine in ethanol. 6 g of penicillin G acylase are then added and the pH is kept constant by addition of triethylamine. When the enzymatic splitting has ended, the acylase is filtered off and the filtrate is brought to pH 2 with concentrated hydrochloric acid. The precipitate formed is filtered off with suction over kieselgur and the filtrate is added dropwise to 2 l of acetone. The desired product precipitates as the hydrochloride and is filtered off with suction and dried. Yield: 3.1 g.

$^1$H-NMR($D_2O$): δ(ppm)=5.39 [1] d, J=5 Hz, 5.16 [1] d, J=5 Hz, 4.80 [1] d, J=13 Hz, 4.14 [1] d, J=13 Hz, 3.85–4.02 [3] m, 3.35–3.72 [7] m, 3.22 [3] s.

(b) Z-7-[2-(2-amino-5-chlorothiazol-4-yl)but-2-enoyl]-amino-3-(4-aminocarbonyl-1-methylpiperazinium)methyl-3-cephem-4-carboxylate 0.56 g (2.56 mmol) of Z-2-(2-amino-5-chlorothiazol-4-yl)but-2-enoic acid is coupled with 0.8 g of 7-amino-3-(4-aminocarbonyl-1-methylpiperazinium)methyl-3-cephem-4-carboxylate hydrochloride analogously to EXAMPLE 17.

Yield after chromatography on Diaion HP 20: 0.5 g $^1$H-NMR(DMSO-$d_6$): δ(ppm)=9.24 [1] d, J=8 Hz, 7.25 [2] bs, 6.40 [1] q, J=8 Hz, 6.32 [2] bs, 5.66 [1] dd, J=8 Hz, J=5 Hz, 5.16 [1] d, J=5 Hz, 5.12 [1] bd, J=13 Hz, 4.01 [1] bd, J=13 Hz, 3.80 [3] m, 3.18–3.65 [7] m, 3.02 [3] s, 1.86 [3] d, J=8 Hz.

EXAMPLE 19

Z-7-[2-(2-amino-5-chlorothiazol-4-yl)but-2-enoyl-]amino-3-(1-methyl-pyrrolidinium)methyl-3-cephem-4-carboxylate

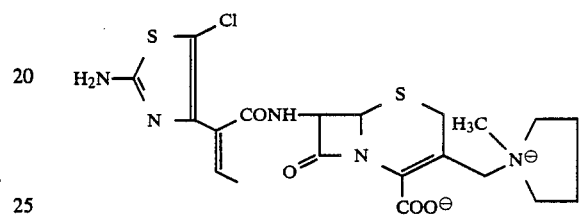

0.5 g (2.29 mmol) of Z-2-(2-amino-5-chlorothiazol-4-yl)but-2-enoic acid is activated in accordance with the instructions of Example 15 and then coupled with a solution of 0.65 g (1.85 mmol) of 7-amino-3-(1-methyl-pyrrolidinium)methyl-3-cephem-4-carboxylate and 0.6 ml triethylamine in 1.5 ml of water. Precipitation from acetone gives 0.68 g=73.9% of theory.

$^1$H-NMR(DMSO-$d_6$): δ(ppm)=9.25 [1] d, J=7 Hz, 7.20 [2] bs, 6.37 [1] q, J=8 Hz, 5.79 [1] dd, J=7 Hz, J=5 Hz, 6.23 [1] d, J=5 Hz, 4.74 [1] d, J=13 Hz, 4.15 [1] d, J=13 Hz, 3.92 [1] d, J=18 Hz, 3.35–3.67 [5] m, 2.91 [3] s, 2.05 [4] m, 1.83 [3] d, J=8 Hz.

EXAMPLE 20

Benzhydryl Z-7-[2-(2-amino-5-chlorothiazol-4-yl)but-2-enoyl-]amino-3-cephem-4-carboxylate

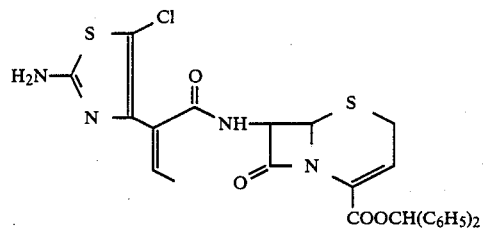

480 mg of Z-2-(2-amino-5-chlorothiazol-4-yl)but-2-enoic acid are activated in accordance with the instructions of Example 15. A solution of 732 mg of benzhydryl 7-β-amino-3-cephem-4-carboxylate in 5 ml of absolute methylene chloride and 360 μl of diisopropylethylamine is added to the cold solution at −50° C. The cooling bath is removed and the mixture is subsequently stirred at room temperature for one hour. The entire batch is poured onto water and extracted several times with methylene chloride. The combined organic extracts are washed with saturated $NaHCO_3$ solution and water, dried over magnesium sulphate and then chromatographed over silica gel (mobile phase: toluene/acetone 8/2). Yield: 330 mg (27%)

¹H-NMR(DMSO-d₆): δ(ppm)=9.32 [1] d, J=9 Hz, 7.20–7.60 [10] m, 6.94 [1] s, 6.78 [1] dd, J=3 Hz, J=5 Hz, 6.42 [1] q, J=8 Hz, 5.92 [1] dd, J=9 Hz, J=5 Hz, 5.18 [1] d, J=5 Hz, 3.68 [2] m, 1.87 [3] d, J=8 Hz.

EXAMPLE 21

Sodium Z-7-[2-(2-amino-5-chlorothiazol-4-yl)but-2-enoyl-]amino-3-cephem-4-carboxylate

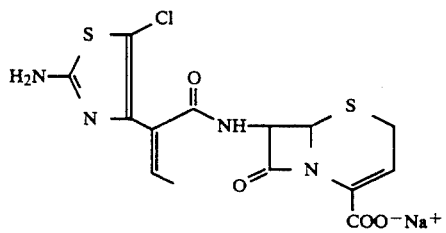

210 mg of benzhydryl Z-7-[2-(2-amino-5-chlorothiazol-4-yl)but-2-enoyl]amino-3-cephem-4-carboxylic acid are dissolved in 3 ml of absolute methylene chloride. After addition of 1.3 ml of anisole and 1.3 ml of trifluoroacetic acid, the mixture is stirred at 0° C. for 25 minutes. The mixture is then concentrated in vacuo, the oily residue is stirred with N-hexane and the solid is filtered off with suction and dissolved with NaHCO₃ in water. The aqueous solution is purified over Diaion HP 20.

Yield: 94 mg (60%)

¹H-NMR(DMSO-d₆): δ(ppm)=9.11 [1] d, J=9 Hz, 7.20 [2] bs, 6.38 [1] q, J=8 Hz, 5.98 [1] m, 5.64 [1] dd, J=5 Hz, J=9 Hz, 4.97 [1] d, J=5 Hz, 3.51 [1] dd, J=2 Hz, J=18 Hz, 3.30 [1] m, 1.85 [3] d, J=8 Hz.

It will be understood that the specification and examples are illustrative but not limitative of the present invention and that other embodiments within the spirit and scope of the invention will suggest themselves to those skilled in the art.

We claim:

1. A compound selected from the group consisting of sodium Z-7-[2-(2-amino-5-chlorothiazol-4-yl)but-2-enoyl]-amino-3-acetoxymethyl-3-cephem-4-carboxylate of the formula

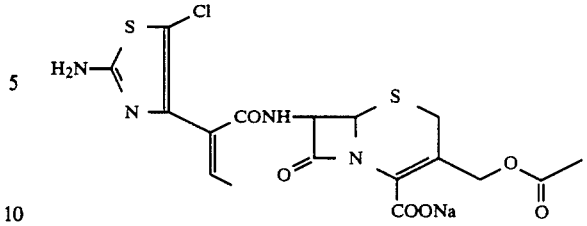

and Z-7-[2-(2-amino-5-chlorothiazol-4-yl)but-2-enoyl]-amino-3-pyridinium-methyl-3-cephem-4-carboxylate of the formula

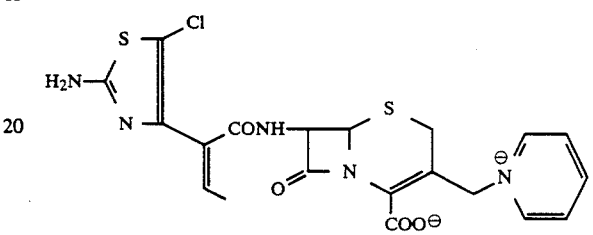

2. A cephalosporin according to claim 1, wherein such compound is sodium Z-7-[2-(2-amino-5-chlorothiazol-4-yl)but-2-enoyl]amino-3-acetoxymethyl-3-cephem-4-carboxylate of the formula

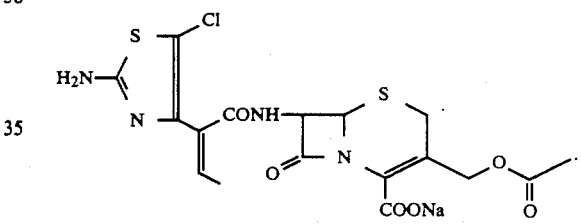

3. A cephalosporin according to claim 1, wherein such compound is Z-7-[2-(2-amino-5-chlorothiazol-4-yl)but-2-enoyl]amino-3-pyridinium-methyl-3-cephem-4-carboxylate of the formula

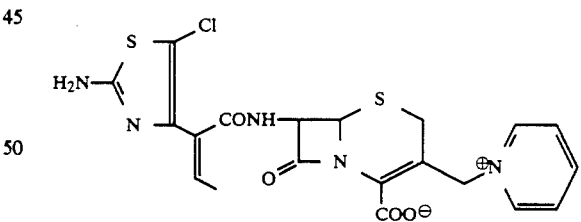

4. An antibacterial composition comprising an antibacterially effective amount of a cephalosporin or salt thereof according to claim 1 and a diluent.

5. A unit dose of a composition according to claim 4 in the form of a tablet, capsule or ampule.

6. A method of combating bacteria which comprises applying bacteria which comprises applying to such bacteria or to a bacteria habitat an antibacterially effective amount of a cephalosporin or salt thereof according to claim 1.

* * * * *